(12) United States Patent
Sin (10) Patent No.: US 7,371,789 B2
(45) Date of Patent: May 13, 2008

(54) ANTI-MICROBIAL PLASTIC COMPOSITION AND WASHING MACHINE COMPRISING THE PARTS MANUFACTURED BY USING THE SAME

(75) Inventor: Soo Hee Sin, Busan (KR)

(73) Assignee: LG Electronics Inc., Seoul (KR)

( * ) Notice: Subject to any disclaimer, the term of this patent is extended or adjusted under 35 U.S.C. 154(b) by 394 days.

(21) Appl. No.: 10/529,386

(22) PCT Filed: May 12, 2004

(86) PCT No.: PCT/KR2004/001093

§ 371 (c)(1),
(2), (4) Date: Mar. 28, 2005

(87) PCT Pub. No.: WO2004/099308

PCT Pub. Date: Nov. 18, 2004

(65) Prior Publication Data

US 2006/0009553 A1    Jan. 12, 2006

(30) Foreign Application Priority Data

| May 12, 2003 | (KR) | ................. 10-2003-0029826 |
| Sep. 2, 2003 | (KR) | ................. 10-2003-0061011 |
| Sep. 2, 2003 | (KR) | ................. 10-2003-0061012 |
| May 12, 2004 | (KR) | ................. 10-2004-0033368 |

(51) Int. Cl.
*C08K 5/45*    (2006.01)

(52) U.S. Cl. ........................... 524/84; 68/72

(58) Field of Classification Search ........ 524/84; 68/232, 72

See application file for complete search history.

(56) References Cited

U.S. PATENT DOCUMENTS 6,437,020 B1 *   8/2002   Amick et al. ............... 523/122

FOREIGN PATENT DOCUMENTS

| JP | 05-025319 | 2/1993 |
| JP | 08-092019 | 4/1996 |
| KR | 1019970004205 B1 | 3/1997 |
| WO | WO 96/14882 | 5/1996 |

\* cited by examiner

*Primary Examiner*—Peter D. Mulcahy
(74) *Attorney, Agent, or Firm*—McKenna Long & Aldridge LLP (57) ABSTRACT

Disclosed are anti-microbial composition, a washing machine including parts manufactured by the same, and a drum washing machine including a stand manufactured by the same. The anti-microbial plastic composition includes 99.0-99.7% of polypropylene and 0.3-1.0% of an anti-microbial master batch, the anti-microbial mater batch having 90% of polypropylene and 5% of isothiazolin compound, and 5% of inorganic compound or 89% of polypropylene, 5% of isothiazolin compound, 5% of inorganic compound, and 1% of silver compound. The isothiazolin compound comprises 4,5-dichloro-2-N-octyl-4-isothiazolin-3-one of chemical formula 1 and 2-N-octyl-4-isothiazolin-3-one of chemical formula 2 at a ratio of 4:1. The inorganic compound is zinc oxide. The washing machine in accordance with the present invention includes the anti-microbial plastic composition, and parts manufactured by the same such that the germs and fungus are prevented from being generated thereof. The drum washing machine in accordance with the present invention includes a cabinet divided into two drawers at the stand thereof.

8 Claims, 6 Drawing Sheets

ANTI-MICROBIAL PLASTIC COMPOSITION AND WASHING MACHINE COMPRISING THE PARTS MANUFACTURED BY USING THE SAME

This application claims priority to Korean Applications 10-2003-0029826, 10-2003-0061011, 10-2003-0061012 and 10-2004-0033368, which were filed in Korea on May 12, 2003, Sep. 2, 2003, Sep. 2, 2003 and May 12, 2004, respectively, the contents of which are incorporated herein by reference in their entirety.

FIELD OF THE INVENTION

The present invention relates to an anti-microbial plastic composition and washing machine including the parts manufactured by using the same, and more particularly, to an anti-microbial plastic composition including 99.0-99.7% of polypropylene and 0.3-1.9% of anti-microbial master batch and a top loading type washing machine and a drum washing machine including the parts manufactured by using the same, and a drum washing machine including a stand manufactured by using the same. The anti-microbial master batch of the present invention includes 90% of polypropylene, 5% of isothiazoline compound and 5% of inorganic compound, or 89% of polypropylene, 5% of isothiazolin compound, 5% of inorganic compound and 1% of silver compound. The isothiazolin compound includes 4,5-dychloro-2-n-octyl-4-isothiazolin-3-one (DCOIT) and 2-N-octyl-4-isothiazolin-3-one (OIT) at a rate of 4:1, and the inorganic compound includes 5% of zinc oxide.

DISCUSSION OF THE RELATED ART

In general, a washing machine is an apparatus for removing various contaminants on clothes and bedclothes by using action of detergent, friction of water current according to rotation of an agitator, and impact applied to laundry by a pulsator. The washing machine automatically sets a washing method by a sensor detecting an amount and a kind of the laundry, supplies wash water to a proper water level according to the amount and kind of the laundry so as to perform washing under a control of a micom.

Meanwhile, methods for operating a conventional washing machine are divided into a washing method of rotating a combination inner tub and dehydration tub by transmitting rotary power from an operating motor to a wash shaft by means of a belt and a pulley for power transmission so as to rotate the pulsator, or to the dehydration axis so as to rotate the combination inner tub and dehydration tub, and a washing method of rotating the combination inner tub and dehydration tub at different speeds for washing and dehydrating, respectively, according to a speed of a BLDC motor.

In addition, there is a washing method of using different steps of power transmission. In other words, the pulsator only is slowly rotated during washing and dehydrating, and the pulsator and the dehydration tub are simultaneously rotated at a high speed during dehydrating.

A method of a permeation washing performing washing by rotating the inner tub or the agitator in a predetermined direction at the high speed while spraying the pumped water current into the inner tub.

Figure 1:
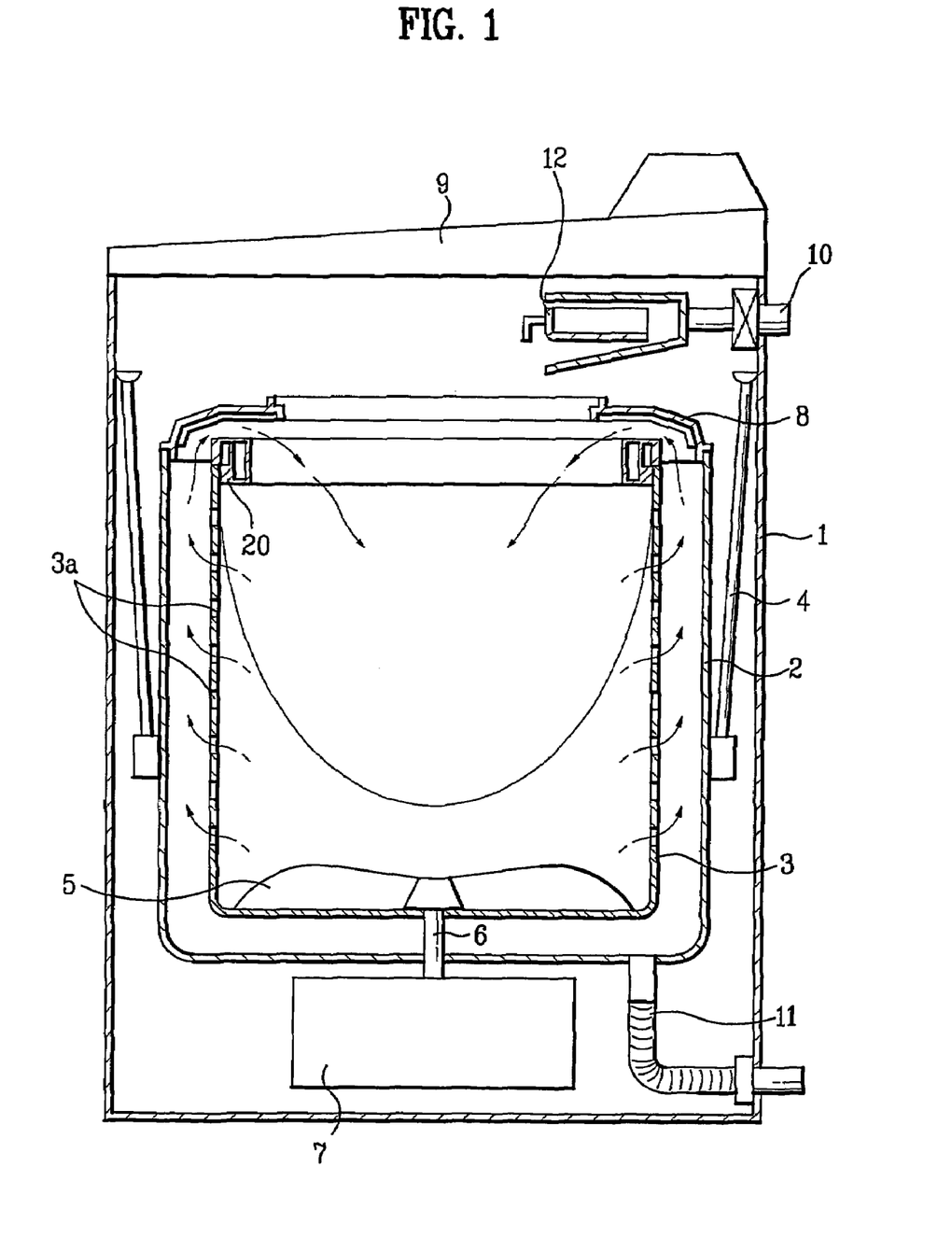
FIG. 1 illustrates a cross-sectional view showing a structure of a conventional top loading washing machine, schematically.

FIG. 1 illustrates an example of a structure of a conventional washing machine and a cross-sectional view showing a structure of a top loading washing machine, schematically.

Referring to the drawing, the top loading type washing machine includes an outer tub being supported by a plurality of supporters 4 in an outer case 1, an inner tub being rotated by a wash shaft 6, receiving laundry and having a plurality of through holes through holes on an inner wall thereof in the outer tub 2, a pulsator 5 integrated with the inner tub 3 at an inner lower part of the inner tub 3, and a motor 7 for rotating the inner tub 3 at a lower end of the outer tub 2.

A tub cover 8 is provided at a top end of the outer tub 2 for supplying wash water risen between the inner tub 3 and the outer tub 2 into the inner tub, a water supplying pipe 10 is provided at a rear side of the outer case 1 and coupled with an outside for supplying the wash water into the inner tub 2, and a drainpipe provided at a lower end of the outer tub 2 for draining out the wash water discharged through the through hole 3a of the inner tub.

A detergent case is provided at a top of the inner tub 3 on the water supplying pipe for automatically inserting the detergent into the inner tub by supplied wash water, and a balance wait 20 is provided at the top end of the inner tub 2 along an circumferential surface thereof for preventing vibration from being generated during dehydrating.

The top loading type washing machine performs washing by rotating the pulsator 5 in the inner tub 3 at the high speed in one direction.

In more detail, the laundry are closely adhered to an inner wall of the inner tub 3 according as the inner tub 3 and the pulsator 5 are rotated at the high speed in one direction. In this instance, the wash water discharged through the through hole 3a of the inner tub is supplied back into the inner tub 3 through the tub cover 8. The contaminants are separated while repeating the process.

In the mean time, contrary to the structure exampled above, the pulsator 5 generating the water current can be separately provided without being integrated with the inner tub 3. In other words, there is a structure wherein the inner tub 3 and the pulsator 5 are rotated in an inverse direction because the inner tub 3 and the pulsator 5 are separately provided.

Furthermore, the there is a washing machine having a recurring series structure wherein the water in the inner tub is pumped and supplied back into the inner tub.

The drum washing machine performs washing by using head generated by the rotation of a rotator provided thereof, resulting in giving same effect of washing laundry by beating with a wash stick and thereby has an advantage of reducing damages by twist of the laundry.

The drum washing machine automatically performs washing, rinsing, dehydrating according to an input program.

In general, the drum washing machine performs washing by using friction between the drum and the laundry, the drum rotated by receiving an operating power of a motor in a state that the detergent, wash water and the laundry are put in the drum. There is almost no damage to laundry, the laundry are not twisted, and gives same effect of washing laundry by beating and rubbing.

Figure 2:
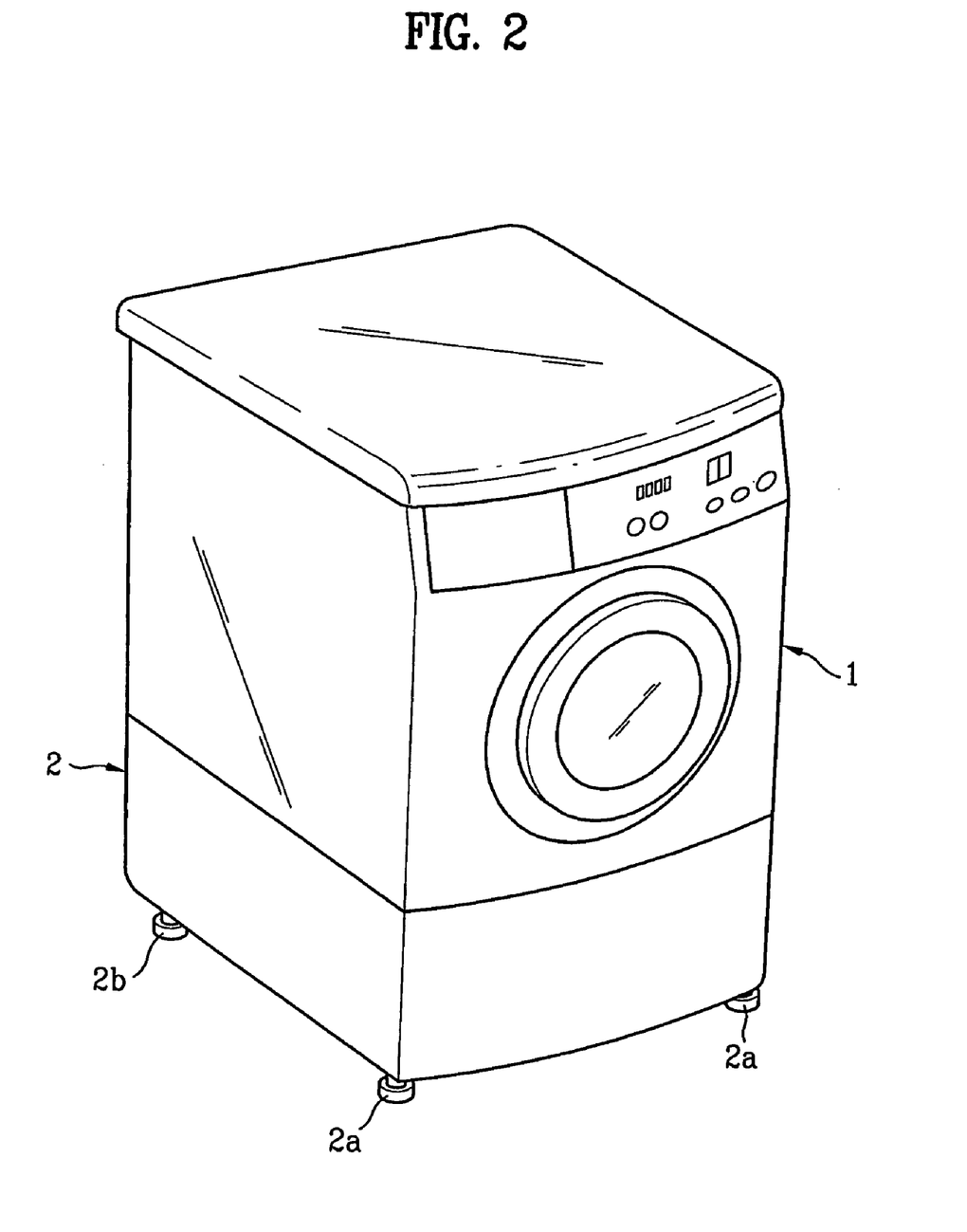
FIG. 2 illustrates a perspective view showing an exterior view of a drum washing machine with a conventional prop.
Figure 3:
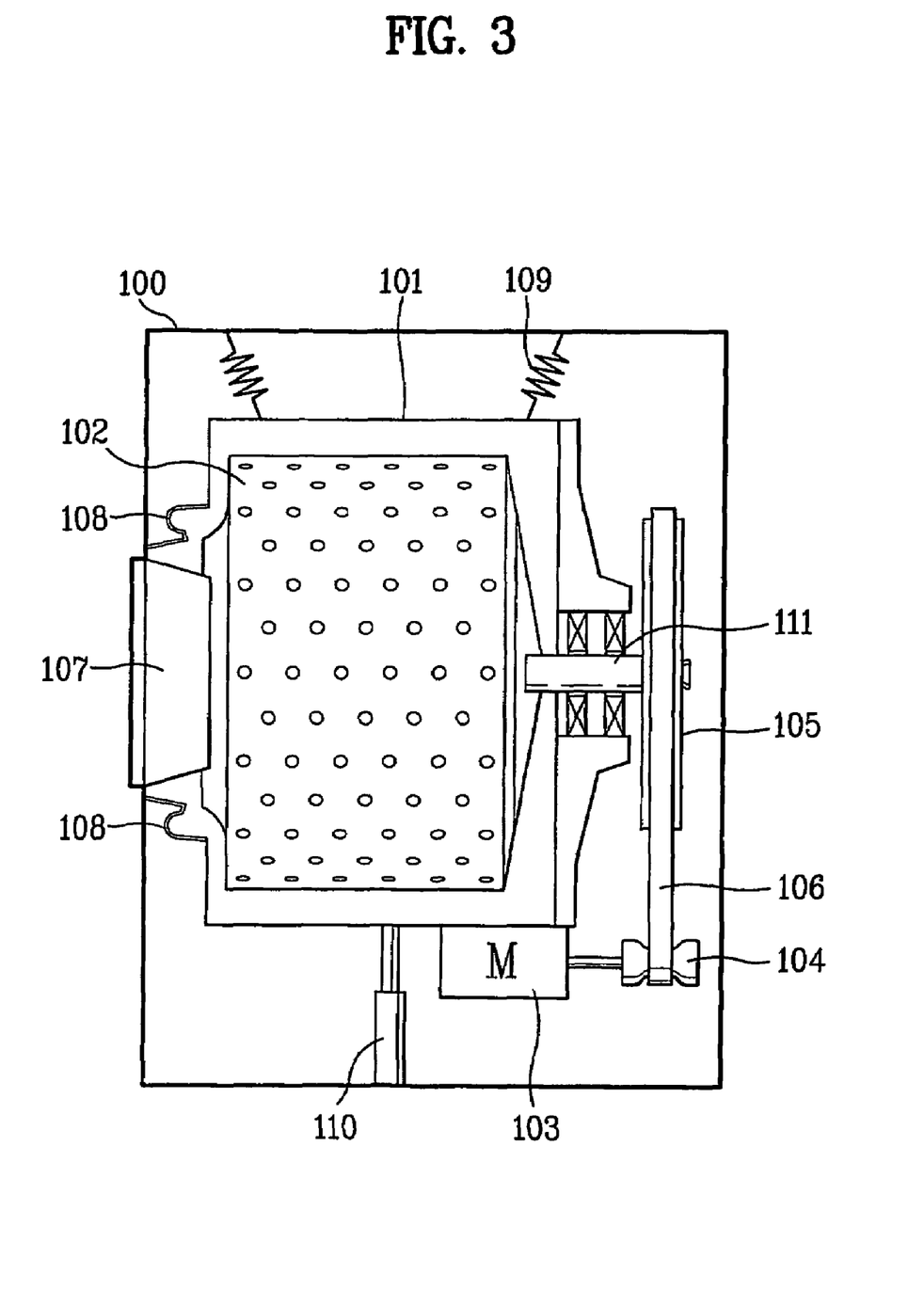
FIG. 3 illustrates a cross-sectional view showing a structure of a conventional drum washing machine, schematically.

FIG. 2 illustrates a perspective view showing an outer appearance of the drum washing machine having a stand in accordance with a related art. FIG. 3 illustrates a cross-sectional view showing a structure of the drum washing machine, schematically. Referring to the drawing, the drum washing machine is briefly described as follows.

As illustrated in FIG. 3, the drum washing machine includes a tub 101 provided inside of a cabinet 100, and a drum rotatably provided in a center of an inside of the tub 101. A motor 103 is provided at a lower part of the tub 101 and a motor pulley is provided at the motor 103.

Meanwhile, a drum axis 111 is provided at a rear of the drum 102 and a 25 drum pulley 105 is provided at the drum axis 111. The motor pulley 104 is coupled to the drum pulley 105 and the motor 103 provided on the drum axis 111, via a belt 106, a power transmission component.

A door 107 is provided in front of the cabinet 100 and a gasket 108 is provided between the door 107 and the tub 101.

A hanging spring 109 is provided between a top inside of the cabinet 100 and a top outside of the tub 111 for supporting the tub 111 and a friction damper 110 is provided between a lower inside of the cabinet 100 and an lower outside of the tub 101 for decreasing vibration of the tub 101 generated during the dehydrating.

The drum washing machine as aforementioned has a disadvantage of lowering a upper body when the laundry are inserted into or withdrawn out from the drum washing machine because the door is provided on a front surface of a main body for inserting or withdrawing the laundry and the location of the door is low.

Therefore, a stand is provided for providing the drum washing machine higher. When the drum washing machine is provided on a rough floor, a stand with a level is provided.

As illustrated in FIG. 2, a stand 2 is provided at a lower part of the drum washing machine 1 for supporting the washing machine and increasing the height thereof. In this instance, the stand 2 includes a leveling leg 2a and a leveling leg 2b respectively at a front and rear side thereof for leveling the drum washing machine 1.

However, inner space of the stand 2 of the drum washing machine 1 is not used, resulting a problem of wasting space. In addition, there is no cabinet for storing detergent, and the detergent is put aside separately, thereby the neighboring space becomes narrower. Particularly, when the detergent is put on top of the drum washing machine 1, the detergent can be fall down through carelessness of a user, resulting a problem of polluting surroundings. Furthermore, the user has to move to look for parts in every case when the user exchange the parts of the drum washing machine 1.

When the parts and the stand of the washing machine is manufactured by plastic, it is often noticed that bacteria or fungus grows on housewares made of plastics although it is easy to think the plastic is a material unpolluted by bacteria.

The plastic has different resistance for each kind. However, when the contaminants are adhered to the plastic, bacteria can grow by using the plastic as nutriment and depletes the plastic. A purpose of the anti-microbial and anti-fungus treatments is making plastic products free from the bacteria. The processing is divided into a melt blending process for adding a chemical in the plastic during molding and a post treatment process for treating a surface after molding. However, the melt blending process is used in most cases of the plastic.

While using a washing machine, a black fungus, a coliform *bacillus*, a *staphylococcus aureus* can grow on the washing machine or the stand thereof. In general, it is easy for the black fungus to generate in a humid and dirty place such as a bath room, a kitchen, or shoe storage. The black fungus is generated on leather articles or old books. The black fungus is a main cause of allergy. Although it is normal that the colon *bacillus* does not show a pathogenic characteristic in an intestine, it generates a cystitis, pyelitis, peritonitis, and septicemia if entered in other places except the intestine. An antigen type coliform *bacillus* such as 26 of 0, 55 of 0, and 111 of 0 is called a deceases-causing colon *bacillus* because it causes infectious diarrhea in an infant to an adult. A *staphylococcus* being a kind of bacteria is a causing germ generating not only food poisoning but also a suppurative disorder such as suppuration, otitis media, and cystitis and is a food poisoning second most common illness after *salmonella* food poisoning and vivrio food poisoning in Korea. There are many kinds of *staphylococcus*. However, only *staphylococcus aureus* generating a yellow pigment causes food poisoning. There are no cases of food poisoning caused by other *staphylococcus* by now. When the fungus grows on a surface, the user feels it is filthy, spoils the appearance, generates a bad odor, and changes an exterior view, resulting in largely decreasing a product value. There is a case of anti-microbial treatment on a purpose of deodorizing indirectly because a elastic enzyme metabolized by germs is a main cause of generating bad odor in many cases. Antibiotics and anti-fungus drug inhibit action of living things such as bacteria and fungus and have a biological activity fundamentally. It is poisonous if the action is large and careful use is necessary. It is thought that there is a low possibility of accidents generated by the plastic products added with the antibiotics and anti-fungus drug because concentration of the drug is very low and the drug itself is fixed in the plastic.

In the mean time, each structural element of the conventional top loading type washing machine and the drum washing machine is normally made of plastic or stainless. In a case the structural element is made of plastic, there is a problem of growing germs such as the bacteria owing to nutrition or contaminants from the detergent or clothes, and a problem of contaminating washed laundry owing to pollution in the washing machine.

Furthermore, there is a problem from hygiene point of view in that the fungus or other germs grow in other structural elements by the wash water spattered during the washing although the other structural parts are employed in the washing machine at a place indirectly related to the washing.

SUMMARY OF THE INVENTION

Accordingly, the present invention is directed to an anti-microbial 25 plastic composition and washing machine including the parts manufactured by using the same that substantially obviates one or more problems due to limitations and disadvantages of the related art.

An object of the present invention is to provide an anti-microbial composition for preventing germs and fungus from being generated.

Another object of the present invention is to provide a washing machine including parts manufactured by using the anti-microbial composition so as to prevent the germs and fungus as well as odor, color change of the appearance, and contaminants of laundry from being generated.

Another object of the present invention is to provide a drum washing machine including a stand manufactured by the anti-microbial composition, and a cabinet divided into two drawers and provided at the stand.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, anti-microbial composition includes 99.0-99.7% of polypropylene, and 0.3-1.0% of an anti-microbial master batch, the anti-microbial master batch having 90% of polypropylene and 5% of isothiazolin compound and 5% of inorganic compound, or 89% of polypropylene, 5% of isothiazolin, 5% of inorganic compound, and 1% of silver compound. The isothiazolin compound comprises 4,5-dichloro-2-n-octyl-4-isothiazolin-3-one of chemical formula 1 and 2-N-octyl-4-isothiazolin-3-one of chemical formula 2 at a ratio of 4:1. The inorganic compound is zinc oxide.

In another aspect of the present invention, the top loading washing machine includes an inner tub, an outer tub, a pulsator, a cover, a detergent box, a water draining hose, and an inner lid, and the drum washing machine includes a tub, a detergent case, a water draining hose, and a lift. The anti-microbial composition used in the washing machines includes 99.0-99.7% of polypropylene, and 0.3-1.0% of an anti-microbial master batch, the anti-microbial master batch having 90% of polypropylene and 5% of isothiazolin compound and 5% of inorganic compound, or 89% of polypropylene, 5% of isothiazolin, 5% of inorganic compound, and 1% of silver compound. The isothiazolin compound comprises 4,5-dichloro-2-n-octyl-4-isothiazolin-3-one (DCOIT) of chemical formula 1 and 2-N-octyl-4-isothiazolin-3-one (OIT) of chemical formula 2 at a ratio of 4:1. The inorganic compound is zinc oxide.

In another aspect of the present invention, the drum washing machine including a stand includes a cabinet divided into two drawers. The stand includes 99.0-99.7% of polypropylene, and 0.3-1.0% of an anti-microbial master batch, the antimicrobial master batch having 90% of polypropylene and 5% of isothiazolin compound and 5% of inorganic compound, or 89% of polypropylene, 5% of isothiazolin, 5% of inorganic compound, and 1% of silver compound. The isothiazolin compound comprises 4,5-dichloro-2-n-octyl-4-isothiazolin-3-one (DCOIT) of chemical formula 1 and 2-N-octyl-4-isothiazolin-3-one (OIT) of chemical formula 2 at a ratio of 4:1. The inorganic compound is zinc oxide.

The parts of the washing machine are manufactured according to a general method by using the anti-microbial plastic composition, the anti-microbial 25 plastic composition including 99.0-99.7% of polypropylene and 0.3-1.0% of an anti-microbial master batch, so as to prevent germs and fungus from being generated during the use of the washing machine. The use of the polypropylene used for the antimicrobial plastic composition is not limited if used in the same field of the present invention. Particularly, it is desirable that a product called "MT42" came into market by LG Chemistry is used. The anti-microbial master batch including 99.0-99.7% of polypropylene and 0.3-1.0% is manufactured according to a general method.

It is desirable that the isothiazolin compound includes 4,5-dichloro-2-noctyl-4-isothiazolin-3-one of chemical formula 1 and 2-N-octyl-4-isothiazolin-3-one of chemical formula 2 at a ratio of 4:1. Except the ratio of 4:1, it is difficult to obtain a 10 sterilizing power in an environment the parts are used thereof. The DCOIT has an intensive sterilizing power and the OIT has a lasting sterilizing power. In the anti-microbial plastic composition in accordance with the present invention, zinc oxide is employed as the inorganic compound.

The anti-microbial master batch in the anti-microbial plastic composition in accordance with the present invention includes silver compound having excellent sterilizing power and anti-microbial effect. Any silver compound can be employed for the present invention without a particular limitation. It is also possible to use the silver alone.

Chemical Formula 1

4,5-dichloro-2-n-octyl-4-isothiazolin-3-one

Chemical Formula 2

2-N-octyl-4-isothhiazolin-3-one

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings.

DETAILED DESCRIPTION OF THE INVENTION

Reference will now be made in detail to the preferred embodiments of the present invention, examples of which are illustrated in the accompanying drawings. Wherever possible, the same reference numbers will be used throughout the drawings to refer to the same or like parts.

Figure 4:
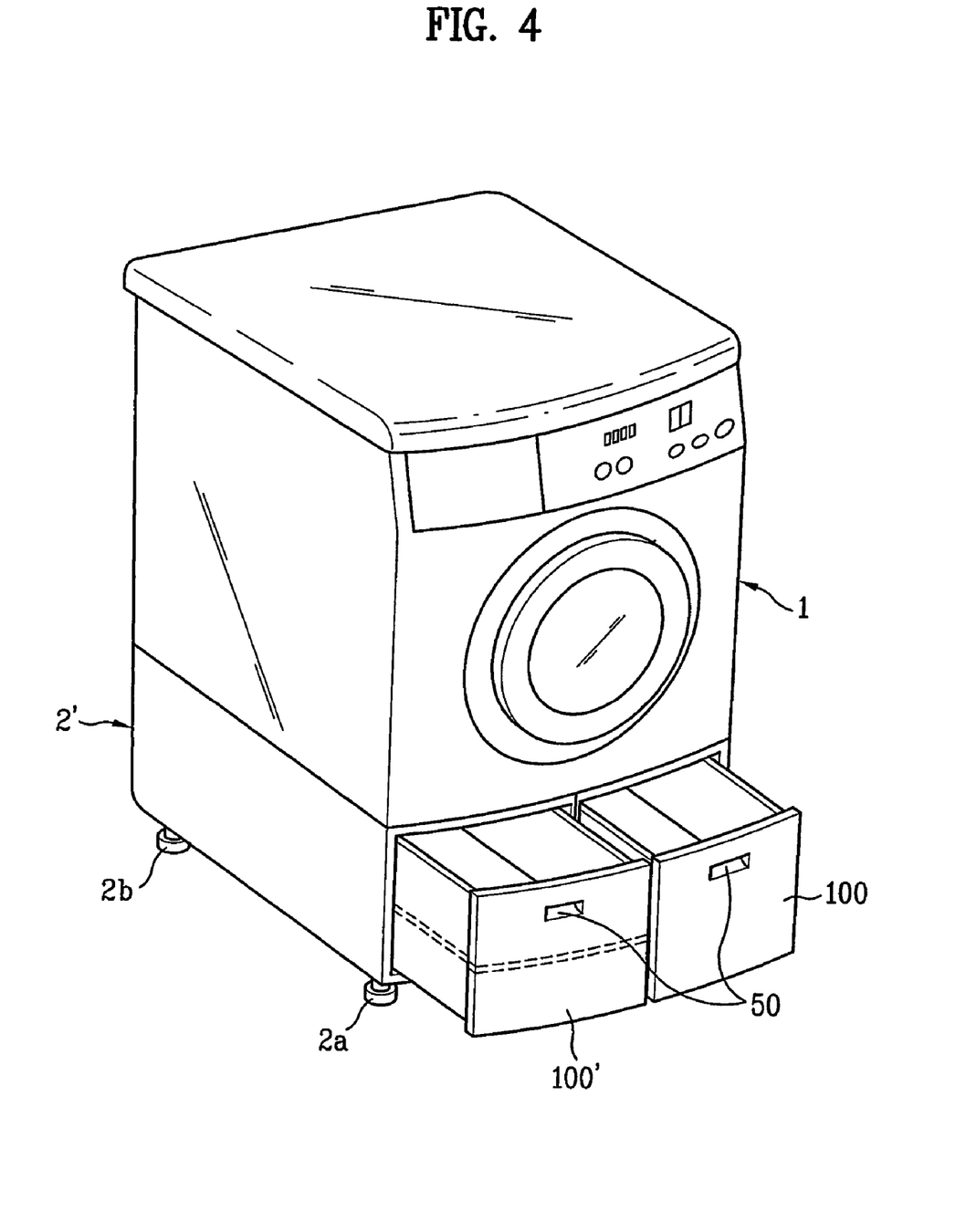
FIG. 4 illustrates a perspective view showing an exterior view of a 20 drum washing machine having a cabinet provided at a stand and divided into two drawers in accordance with the present invention.

FIG. 4 illustrates a perspective view showing an exterior view of a drum washing machine having a cabinet provided at the stand and divided into two drawers in accordance with the present invention. As illustrated in FIG. 4, the present invention includes a drum washing machine 1, a stand 2' for securing a height of the drum washing machine I, and leveling, and a cabinet 100 and 100' provided at the stand 2' and divided in a form of a drawer. Meanwhile, the present invention is not limited to the abovementioned embodiment, but various modifications and variations can be made in the present invention without departing from the spirit or scope of the inventions.

For example, in the abovementioned embodiment, there are two drawers at the prop. However, the drawers can be two or more according to a size of the stand and things in the drawers are categorized by kind appropriately.

EMBODIMENT 1

An anti-microbial master batch is produced by absorbing 5% of inorganic compound that is zinc oxide from 5% of isothiazolin compound mixed with 90% of polypropylene and DCOIT and OIT at a ratio of 4:1. The parts of the washing machine are manufactured by mixing 0.3% of the anti-microbial master batch with 99.7% of MT42.

EMBODIMENT 2

The parts of the washing machine are manufactured in a same way as the embodiment 1 except that 0.4% of the anti-microbial master batch is mixed with 99.6% of MT42.

EMBODIMENT 3

The parts of the washing machine are manufactured in a same way as the embodiment 1 except that 0.5% of the anti-microbial master batch is mixed with 99.5% of MT42.

EMBODIMENT 4

The parts of the washing machine are manufactured in a same way as the embodiment 1 except that 0.6% of the anti-microbial master batch is mixed with 99.4% of MT42.

EMBODIMENT 5

The parts of the washing machine are manufactured in a same way as 20 the embodiment 1 except that 0.7% of the anti-microbial master batch is mixed with 99.3% of MT42.

EMBODIMENT 6

The parts of the washing machine are manufactured in a same way as the embodiment 1 except that 0.8% of the anti-microbial master batch is mixed with 99.2% of MT42.

EMBODIMENT 7

The parts of the washing machine are manufactured in a same way as the embodiment 1 except that 0.9% of the anti-microbial master batch is mixed with 99.1%

EMBODIMENT 8

The parts of the washing machine are manufactured in a same way as the embodiment 1 except that 1.0% of the anti-microbial master batch is mixed with 99.0% of MT42.

EMBODIMENT 9

The anti-microbial master batch are manufactured by absorbing 5% of inorganic compound, that is zinc oxide, and 1% of silver from 5% of isothiazolin compound mixed with 80% of polypropylene and DCOIT and OIT at a ratio of 4:1. The parts of the washing machine are manufactured by mixing 0.3% of the anti-microbial master batch with 99.7% of MT42.

EMBODIMENT 10

The parts of the washing machine are manufactured in a same way as the embodiment 9 except that 0.4% of the anti-microbial master batch is mixed with 99.6% of MT42.

EMBODIMENT 11

The parts of the washing machine are manufactured in a same way as the embodiment 9 except that 0.5% of the anti-microbial master batch is mixed with 99.5% of MT42.

EMBODIMENT 12

The parts of the washing machine are manufactured in a same way as the embodiment 9 except that 0.6% of the anti-microbial master batch is mixed with 99.4% of MT42.

EMBODIMENT 13

The parts of the washing machine are manufactured in a same way as the embodiment 9 except that 0.7% of the anti-microbial master batch is mixed with 99.3% of MT42.

EMBODIMENT 14

The parts of the washing machine are manufactured in a same way as the embodiment 9 except that 0.8% of the anti-microbial master batch is mixed with 99.2% of MT42.

EMBODIMENT 15

The parts of the washing machine are manufactured in a same way as the embodiment 9 except that 0.9% of the anti-microbial master batch is mixed with 99.1% of MT42.

EMBODIMENT 16

The parts of the washing machine are manufactured in a same way as the embodiment 9 except that 1.0% of the anti-microbial master batch is mixed with 99.0% of MT42.

COMPARATIVE EXAMPLE 1

The parts of the washing machine are manufactured by using 0.4% of the anti-microbial master batch, Chemcide 10, 10'-oxybisp henoxarsine (OBPA) that is on the market. The Chemcide includes 95% of polypropylene and 5% of OBPA.

COMPARATIVE EXAMPLE 2

The parts of the washing machine are manufactured by a same way as the embodiment 1 except that Ag and Zn are used instead of zinc oxide.

The antibiosis of the compound of the parts obtained from the embodiment and comparative example before molding the parts is tested for testing the antibiosis of the parts in accordance with the present invention.

Halo Test: $3 \times 10^6$ of *staphylococcus* (*S. aureus*) and coliform *bacillus* (*E. coli*) ate coated on the NA placement on each plate, the compound of the stand manufactured in the first to sixteenth embodiments and the first to second comparative examples, before molding the prop, is laid out in a size of 2.5×2.5 m, and cultured for 24 hours.

Also in the case of the fungus, 200 μl of the fungus (*A. niger*) is coated on a PDA plate and the sample is laid out in the size of 2.5×2.5 cm, and cultured at 25° C. for 24 hours. Through whether a clear zone is created around the sample, a function of the antibiotics is determined.

Figure 5:
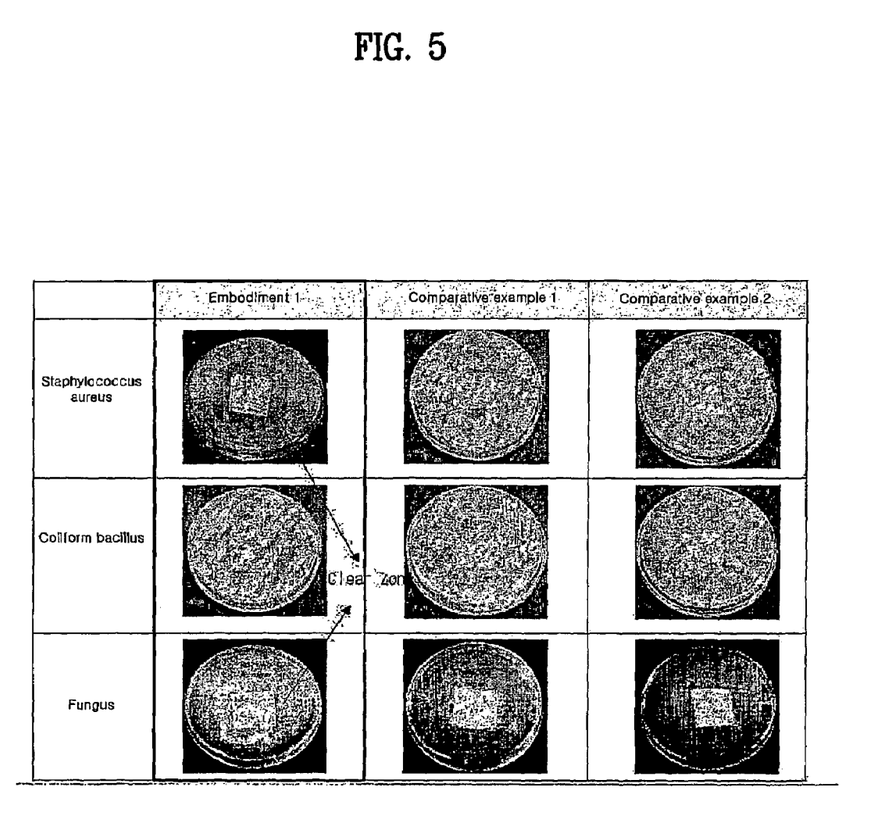
FIG. 5 illustrates a picture of test result after antibiosis of an antimicrobial plastic composition is tested according to a Halo Test in accordance with the present invention.

The test result used the Halo test is described in Table I and FIG. 5. The results of the embodiments 1-8 and 9-16 are all the same, and only the results of embodiment 1 and the comparative example 1 and 2 are disclosed.

TABLE 1

|  | Conform bacillus | Staphylococcus aureus | | | | | Fungus | | | |
|---|---|---|---|---|---|---|---|---|---|---|
| Embodiment 1 | 1 | 1.1 | 1.2 | 1.2 | 1.5 | 0.7 | 0.8 | 0.8 | 0.9 | 0.9 |
| Embodiment 2 | 1 | 1.1 | 1.2 | 1.2 | 1.5 | 0.7 | 0.8 | 0.8 | 0.9 | 0.9 |
| Embodiment 3 | 1 | 1.1 | 1.2 | 1.2 | 1.5 | 0.7 | 0.8 | 0.8 | 0.9 | 0.9 |
| Embodiment 4 | 1 | 1.1 | 1.2 | 1.2 | 1.5 | 0.7 | 0.8 | 0.8 | 0.9 | 0.9 |
| Embodiment 5 | 1 | 1.1 | 1.2 | 1.2 | 1.5 | 0.7 | 0.8 | 0.8 | 0.9 | 0.9 |
| Embodiment 6 | 1 | 1.1 | 1.2 | 1.2 | 1.5 | 0.7 | 0.8 | 0.8 | 0.9 | 0.9 |
| Embodiment 7 | 1 | 1.1 | 1.2 | 1.2 | 1.5 | 0.7 | 0.8 | 0.8 | 0.9 | 0.9 |
| Embodiment 8 | 1 | 1.1 | 1.2 | 1.2 | 1.5 | 0.7 | 0.8 | 0.8 | 0.9 | 0.9 |
| Embodiment 9 | 1 | 1.1 | 1.2 | 1.2 | 1.5 | 0.7 | 0.8 | 0.8 | 0.9 | 0.9 |
| Embodiment 10 | 1 | 1.1 | 1.2 | 1.2 | 1.5 | 0.7 | 0.8 | 0.8 | 0.9 | 0.9 |
| Embodiment 11 | 1 | 1.1 | 1.2 | 1.2 | 1.5 | 0.7 | 0.8 | 0.8 | 0.9 | 0.9 |
| Embodiment 12 | 1 | 1.1 | 1.2 | 1.2 | 1.5 | 0.7 | 0.8 | 0.8 | 0.9 | 0.9 |
| Embodiment 13 | 1 | 1.1 | 1.2 | 1.2 | 1.5 | 0.7 | 0.8 | 0.8 | 0.9 | 0.9 |
| Embodiment 14 | 1 | 1.1 | 1.2 | 1.2 | 1.5 | 0.7 | 0.8 | 0.8 | 0.9 | 0.9 |
| Embodiment 15 | 1 | 1.1 | 1.2 | 1.2 | 1.5 | 0.7 | 0.8 | 0.8 | 0.9 | 0.9 |
| Embodiment 16 | 1 | 1.1 | 1.2 | 1.2 | 1.5 | 0.7 | 0.8 | 0.8 | 0.9 | 0.9 |
| Embodiment 1 | 0 | 0 | 0 | 0.3 | 0.4 | 0.05 | 0.05 | 0.1 | 0.1 | 0.1 |
| Embodiment 2 | 0.05 | 0.1 | 0.1 | 0.2 | 0.2 | — | | | | |

"—" means no effect, and a unit is cm.

As illustrated in Table I and FIG. 5, the clear zone in the embodiment 1 is far larger than that in the comparative examples 1 and 2.

Shake Flask test: the *staphylococcus aureus* and the fungus inoculated into LB liquid in an Erlenmeyer flask, in this case, 10 of the compound sample in the embodiment and the comparative example are added thereto in a size of 1×1 cm, and shake-cultured at 37° for 24 hours.

Before inoculating the sample, 100 μl, 10 μl, and 1 μl are taken from the flask and coated on the NB plate for making a control group.

After the culture, 100 μl and 10 μl of the culture fluid are taken and coated on the NB plate for measuring the number of germs. The result is disclosed in Table 2.

TABLE 2

| Kind of germs | Sample | Unit | Number of germs at first stage | After 24 hours | Rate of restraint —(%) |
|---|---|---|---|---|---|
| Staphylo­coccus aureus | Embodiment 1 | CFU/ml | $5.0 \times 10^5$ | <1 | 99.9 |
| | Embodiment 2 | CFU/ml | $5.0 \times 10^5$ | <1 | 99.9 |
| | Embodiment 3 | CFU/ml | $5.0 \times 10^5$ | <1 | 99.9 |
| | Embodiment 4 | CFU/ml | $5.0 \times 10^5$ | <1 | 99.9 |
| | Embodiment 5 | CFU/ml | $5.0 \times 10^5$ | <1 | 99.9 |
| | Embodiment 6 | CFU/ml | $5.0 \times 10^5$ | <1 | 99.9 |
| | Embodiment 7 | CFU/ml | $5.0 \times 10^5$ | <1 | 99.9 |
| | Embodiment 8 | CFU/ml | $5.0 \times 10^5$ | <1 | 99.9 |
| | Embodiment 9 | CFU/ml | $5.0 \times 10^5$ | <1 | 99.9 |
| | Embodiment 10 | CFU/ml | $5.0 \times 10^5$ | <1 | 99.9 |
| | Embodiment 11 | CFU/ml | $5.0 \times 10^5$ | <1 | 99.9 |
| | Embodiment 12 | CFU/ml | $5.0 \times 10^5$ | <1 | 99.3 |
| | Embodiment 13 | CFU/ml | $5.0 \times 10^5$ | <1 | 99.9 |
| | Embodiment 14 | CFU/ml | $5.0 \times 10^5$ | <1 | 99.9 |
| | Embodiment 15 | CFU/ml | $5.0 \times 10^5$ | <1 | 99.9 |
| | Embodiment 16 | CFU/ml | $5.0 \times 10^5$ | <1 | 99.9 |
| | Comparative example 1 | CFU/ml | $5.0 \times 10^5$ | <1 | 99.9 |
| | Comparative example 2 | CFU/ml | $5.0 \times 10^5$ | <1 | 99.9 |
| Coliform bacillus | Embodiment 1 | CFU/ml | $6.0 \times 10^5$ | $6.4 \times 10^8$ | 14.6 |
| | Embodiment 2 | CFU/ml | $6.0 \times 10^5$ | $6.4 \times 10^8$ | 14.6 |
| | Embodiment 3 | CFU/ml | $6.0 \times 10^5$ | $6.4 \times 10^8$ | 14.6 |
| | Embodiment 4 | CFU/ml | $6.0 \times 10^5$ | $6.4 \times 10^8$ | 14.6 |
| | Embodiment 5 | CFU/ml | $6.0 \times 10^5$ | $6.4 \times 10^8$ | 14.6 |
| | Embodiment 6 | CFU/ml | $6.0 \times 10^5$ | $6.4 \times 10^8$ | 14.6 |
| Coliform bacillus | Embodiment 7 | CFU/ml | $6.0 \times 10^5$ | $6.4 \times 10^8$ | 14.6 |
| | Embodiment 8 | CFU/ml | $6.0 \times 10^5$ | $6.4 \times 10^8$ | 14.6 |
| | Embodiment 9 | CFU/ml | $6.0 \times 10^5$ | $6.4 \times 10^8$ | 14.6 |
| | Embodiment 10 | CFU/ml | $6.0 \times 10^5$ | $6.4 \times 10^8$ | 14.6 |
| | Embodiment 11 | CFU/ml | $6.0 \times 10^5$ | $6.4 \times 10^8$ | 14.6 |
| | Embodiment 12 | CFU/ml | $6.0 \times 10^5$ | $6.4 \times 10^8$ | 14.6 |
| | Embodiment 13 | CFU/ml | $6.0 \times 10^5$ | $6.4 \times 10^8$ | 14.6 |
| | Embodiment 14 | CFU/ml | $6.0 \times 10^5$ | $6.4 \times 10^8$ | 14.6 |
| | Embodiment 15 | CFU/ml | $6.0 \times 10^5$ | $6.4 \times 10^8$ | 14.6 |
| | Embodiment 16 | CFU/ml | $6.0 \times 10^5$ | $6.4 \times 10^8$ | 14.6 |
| | Comparative example 1 | CFU/ml | $6.0 \times 10^5$ | $6.4 \times 10^8$ | 15.3 |
| | Comparative example 2 | CFU/ml | $6.0 \times 10^5$ | $5.2 \times 10^8$ | 31.3 |

As illustrated in Table 2, in the sample according to the embodiments 1-16, the number of *staphylococcus aureus* is decreased to less than 1 and showed 99% of restraint.

The sample drip test: As a test for confirming the anti-microbial effect against the fungus on a surface of the liquid crystal, one drop of PDA is dropped on the liquid crystal. To this solution, the fungus (*A. niger*) is inoculated and cultured at 25° C. for 72 hours.

Figure 6:
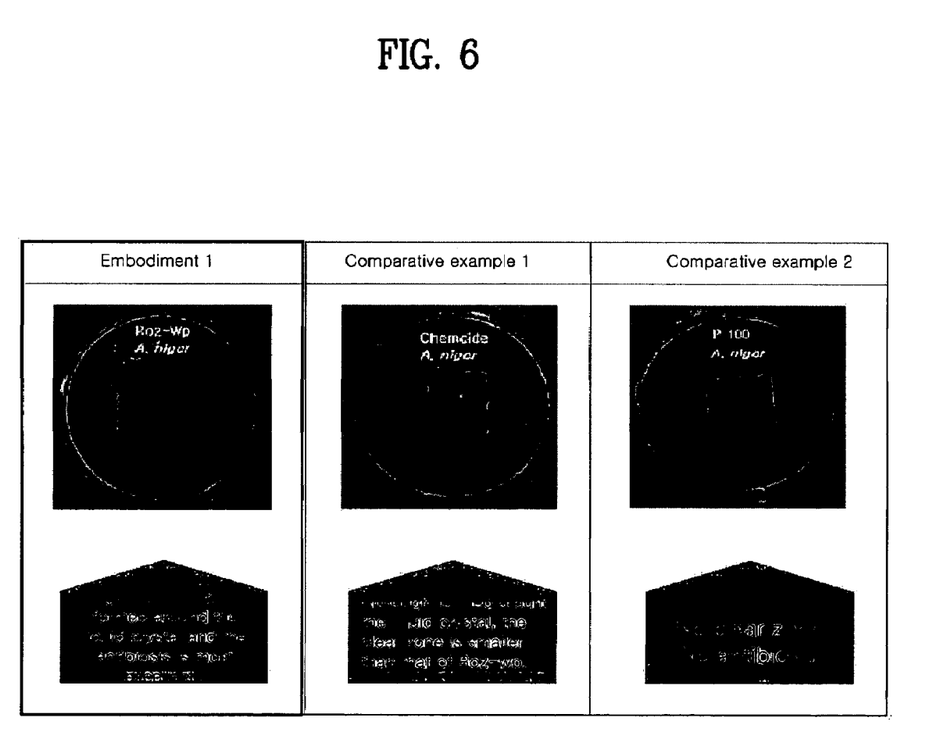
FIG. 6 illustrates a picture of a test result showing antibiosis of an anti-5 microbial plastic composition is tested according to a drip test in accordance with the present invention.

The embodiment 1-16 and the comparative examples 1 and 2 are tested by the sample drip test, and the results are all the same in the embodiments, therefore only the results of the embodiment 1 and the comparative examples 1 and 2 are disclosed in FIG. 6.

The antibiosis test results are almost the same in the embodiments, and thus using 0.3% of the anti-microbial master batch is the most economical in accordance with the present invention.

In the mean time, the present invention is not limited to the above-mentioned embodiments, and various modifications and variations can be made in the present invention without departing from the spirit or scope of the inventions.

As aforementioned, owing to germs such as a tick and bacteria inhabit on the laundry or contaminants or nutriment from the laundry, the inside of the washing machine or the wash water is polluted. By replacing the parts at the place in contact with the wash water or moisture with the antmicrobial plastic composition, obtained is not only an effect of cleaning the inside of the washing machine but also maintaining the cleanness of the laundry because the inhibition of the fungus and other germs are prevented.

It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents.

In other words, the anti-microbial plastic in accordance with the present invention is applied to parts of the top loading type washing machine such as the inner tub the outer tub, the pulsator, the cover, the detergent box, the water draining hose, and an inner lid (structure of guiding water current, inner bin) and the parts of the drum washing machine such as the tub, the detergent case, the water draining hose, the lift, the prop, and plastic parts in contact with wash Water or water. The antimicrobial substances are not limited to one kind.

INDUSTRIAL APPLICABILITY

The present invention is an anti-plastic composition, which is used to parts of washing machines including the top loading type washing machine and the drum washing machine. During the use of the washing machine manufactured by the anti-microbial plastic composition, germs and fungus are prevented from being generated. Furthermore, a cabinet is provided at the stand of the drum washing machine and divided into two drawers.

What is claimed is:

1. An anti-microbial composition, comprising:
    99.0-99.7% of polypropylene; and
    0.3-1.0% of an anti-microbial master batch, the anti-microbial master batch having 89% of polypropylene, 5% of isothiazolin compound, 5% of inorganic compound, and 1% of silver compound, wherein the inorganic compound is different from the silver compound and the isothiazolin compound comprises 4,5-dichloro-2-N-octyl-4-isothiazolin-3-one of chemical formula 1 and 2-N-octyl-4-isothiazolin-3-one of chemical formula 2 at a ratio of 4:1.

Chemical Formula 1

4,5-dichloro-2-N-octyl-4-isothiazolin-3-one

Chemical Formula 2

2-N-octyl-4-isothhiazolin-3-one.

2. The anti-microbial composition as claimed in claim 1, wherein the inorganic compound is zinc oxide.

3. A top loading type washing machine comprises pans manufactured by the anti-microbial plastic composition according to claim 1.

4. A drum washing machine comprises parts manufactured by the anti-microbial plastic composition according to claim 1.

5. A drum washing machine comprises a stand manufactured by the anti-microbial plastic composition according to claim 1.

6. A drum washing machine as claimed in claim 5, further comprising a cabinet divided into two drawers.

7. An anti-microbial composition, comprising:
    99.0-99.7% polypropylene; and
    0.3-1.0% of an anti-microbial master batch, the anti-microbial master batch having 90% of polypropylene and 5% of an isothiazolin compound and 5% of an inorganic compound, wherein the inorganic compound is different from a silver compound and the isothiazolin compound comprises 4,5-dichloro-2-N-octyl-4-isothiazolin-3-one of chemical formula 1 and 2-N-octyl-4-isothiazolin-3-one of chemical formula 2 at a ratio of 4:1.

Chemical Formula 1

4,5-dichloro-2-N-octyl-4-isothiazolin-3-one

Chemical Formula 2

2-N-octyl-4-isothhiazolin-3-one.

8. The anti-microbial composition as claimed in claim 7, wherein the inorganic compound is zinc oxide.

* * * * *